(12) United States Patent
Laredo et al.

(10) Patent No.: US 7,625,581 B2
(45) Date of Patent: *Dec. 1, 2009

(54) TISSUE SCAFFOLDS FOR USE IN MUSCOLOSKELETAL REPAIRS

(75) Inventors: Walter R. Laredo, Hillsborough, NJ (US); Alireza Rezania, Hillsborough, NJ (US); Mark C. Zimmerman, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 482 days.

This patent is subject to a terminal disclaimer.

(21) Appl. No.: 10/742,136

(22) Filed: Dec. 19, 2003

(65) Prior Publication Data

US 2005/0147642 A1     Jul. 7, 2005

(51) Int. Cl.
*A61K 9/14* (2006.01)
*A61K 31/70* (2006.01)

(52) U.S. Cl. .................................. 424/426; 514/54
(58) Field of Classification Search ................ 424/423, 424/426, 486, 428; 536/54, 55.3
See application file for complete search history.

(56) References Cited

U.S. PATENT DOCUMENTS

| | | | |
|---|---|---|---|
| 4,713,448 A | 12/1987 | Balazs | |
| 4,736,024 A * | 4/1988 | Della Valle et al. | ......... 536/55.3 |
| 4,851,521 A | 7/1989 | della Valle et al. | |
| 5,017,229 A | 5/1991 | Burns et al. | |
| 5,336,767 A | 8/1994 | della Valle et al. | |
| 5,356,883 A | 10/1994 | Kuo et al. | |
| 5,658,582 A | 8/1997 | Dorigatti et al. | |
| 5,735,863 A | 4/1998 | della Valle et al. | |
| 5,925,626 A | 7/1999 | della Valle et al. | |
| 7,091,191 B2 * | 8/2006 | Laredo et al. | ............. 514/54 |
| 2002/0119179 A1 * | 8/2002 | Rezania et al. | ............. 424/426 |
| 2002/0131989 A1 * | 9/2002 | Brown et al. | ............. 424/428 |

FOREIGN PATENT DOCUMENTS

| | | |
|---|---|---|
| WO | WO 9515168 A1 | 8/1995 |
| WO | WO 9745532 A1 | 4/1997 |

OTHER PUBLICATIONS

Bulpitt,P.; Aeschlimann D. "New strategy for chemical modificaiton of hyaluronic acid; preparation of functionalized derivatives and their use in the formation of novel biocompatible hydrogels," Journal of Biomedical Materials (1999), 47, 152-169.

Luo, Y.; Kirker, K.R.; Prestwich, G.D. "Cross-inked hyaluronic acid hydrogel films; new ibomaterials for drug delivery," Journal of Controlled Release (2000) , 69, 169-184.

Drury, J.L.; Mooney, D.J. "Hydrogels for tissue engineering; scaffold design variables and applications," Biomaterials (2003), 24, 4337-4351.

Halbleib,M.; Skurk,T.; de Luca, C.; von Heimburg, D.; Hauner, H. "Tissue engineering of white adipose tissue using hyaluronic acid-based scaffolds. I: Invitro differentiation of human adipocyte precursor cells on scaffolds," Biomaterials (2003), 24, 3125-3132.

Dausse, Y.; Grossin, L.; Miralles, G.; Peletier, S.; Mainard, D.; Hubert, P.; Baptise, D.; Gillet, P.; Dellacherie, E; Netter, P.; Payan, E. "Cartilage repair using new polysaccharidic biomaterials; macrosocpic, histological and biochemical approaches in a rat model of cartilage defect," Osteoarthritic and Cartilage (Jan. 2003), 11, 16-28.

Miilella, E.; Brescia, E.; Massaro, C.; Ramires, P.,A.; Miglietta, M.R.; Fiori V.; Aversa, P. "Physico-chemical properties and degradability of non-woven hyaluronan benzylic esters as tissue engineering scaffolds", Biomaterials (2001), 23, 1053-1063.

Pianigiani, E.; Andreassi, A.; Taddeucci, P.; Allessandrini, C.; Fimiani, M. Andressi, L. "A new model for studying differentiation and growth of epidermal cultures on hyaluronan-based carrier," Biomaterials (1999), 20, 1689-1694.

Prestwich, G.D.; Marecak, D.M.; Marecek , J.F.; Vercuysse, K.P.; Ziebell, M.R. "Controlled chemical modificatoin of hyaluronic acid: synthesis, appications and biodegradation of hydrazide derivatives", Journal of Controlled Release (1998), 53, 93-103.

Birotto,D.; Urbani,S.; Bru, P., Prnier, D.; Barbucci, R. Abatangelo, G. "Tissue-specific gene expression in chondrocytes grown on three-dimensional hyaluronic acid scaffolds,"Biomateroals (203), 24, 3265-3275.

Cascone, M.G.; Sim, B.; Downes, S. "Blends of synthetic and natural polymers as drug delivery systems for growth hormone," Biomaterails (1995), 16, 569-74.

* cited by examiner

*Primary Examiner*—Michael G Hartley
*Assistant Examiner*—Jagadishwar R Samala
(74) *Attorney, Agent, or Firm*—Roberts, Mlotkowski, Safran & Cole, P.C.

(57) ABSTRACT

The present invention includes a tissue scaffold suitable for use in repair and/or regeneration of musculoskeletal tissue when implanted in a body that includes a porous substrate made from a biodegradable, hydrophobic polymer having a modified hyaluronic acid complex dispersed on the surface of and/or, where the modified hyaluronic acid complex is insoluble in water, yet soluble in mixtures of organic and aqueous solvents in which the hydrophobic polymer is soluble.

18 Claims, 3 Drawing Sheets

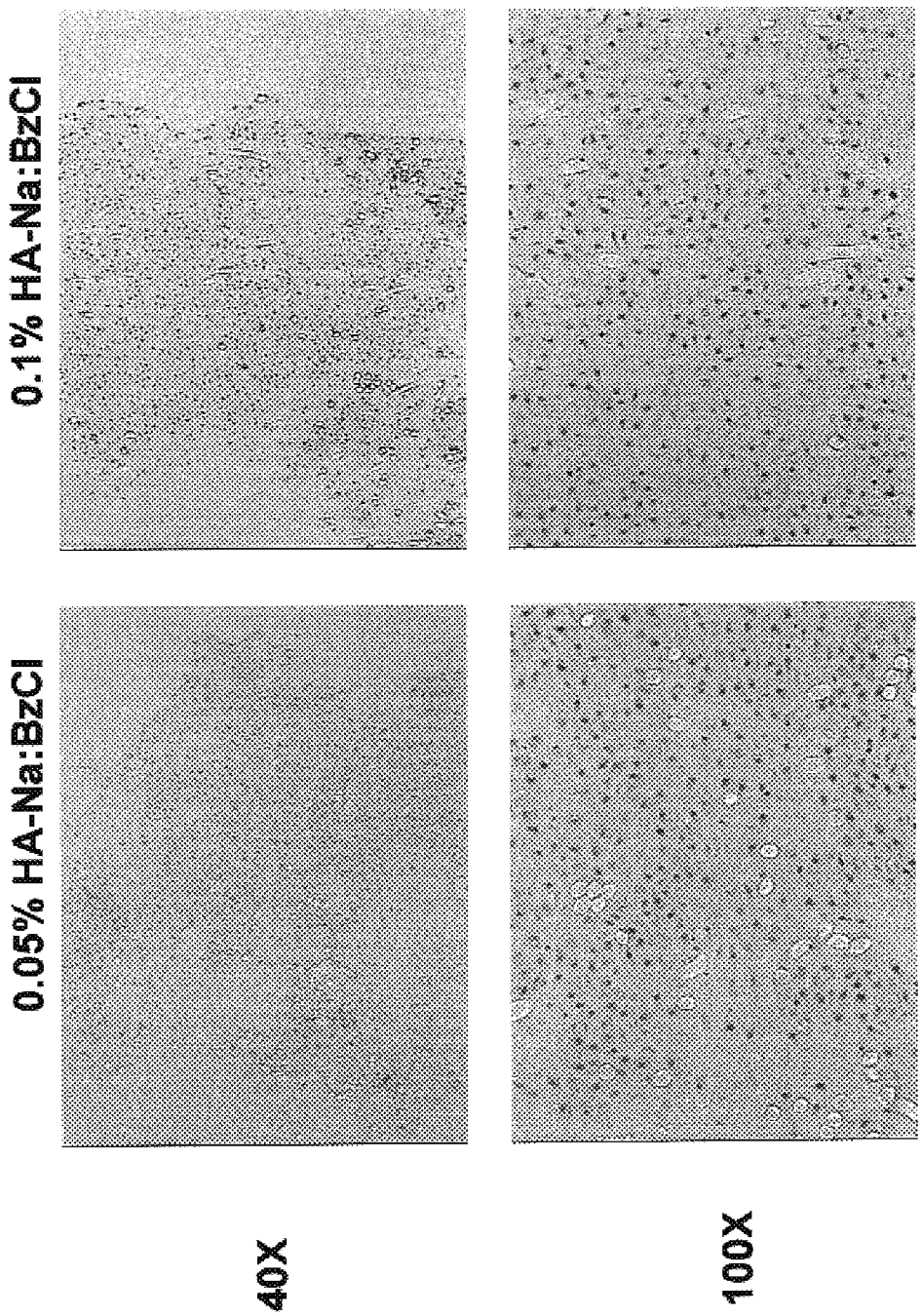

TISSUE SCAFFOLDS FOR USE IN MUSCOLOSKELETAL REPAIRS

FIELD OF THE INVENTION

The present invention is directed to tissue scaffolds suitable for use in tissue repair and/or regeneration and that are composed of a porous substrate made from a biodegradable, synthetic polymer and that have a hydrophobic hyaluronic acid complex incorporated therewith.

BACKGROUND OF THE INVENTION

There is a clinical need for biocompatible and biodegradable structural matrices that facilitate tissue infiltration to repair/regenerate diseased or damaged tissue. Previous attempts have used a number of naturally occurring, as well as synthetic biodegradable materials as scaffolds in the tissue repair process.

One class of biodegradable and biocompatible materials is the family of polysaccharides. One particular polysaccharide used for scaffolds is hyaluronic acid (HA). HA is a naturally-occurring linear polysaccharide comprised of D-glucuronic acid and N-acetyl-D-glucosamine. The polyanionic polymer has a range of molecular weight of from 1,000-10,000,000 Daltons. The use of purified HA has become common practice for treatments such as corneal transplantation, viscosupplementation of the knee, anti-adhesive barriers in spinal surgeries and wound healing applications.

HA has been explored as a scaffold to enhance the repair of tissue. However, the poor physical properties of natural HA and its rapid resorption by the body has restricted its use to applications where a structurally sound scaffold is not required.

Numerous groups have attempted to modify HA to obtain a more robust and water insoluble biopolymer for tissue engineering applications. One line of modifications involved the use of cross-linking agents. These cross-linking agents include formaldehyde, glutaraldehyde, vinyl sulphone, bis-carbodiimides, poly-functional epoxides, glycidyl ether, photocurable cinnamic acid derivatives and adipic dihydrazide. However, they are concerns regarding the potential toxicity of some of the cross-linking agents.

Alternatively, HA derivatives have been obtained by targeting specific functional groups of HA, such as carboxyl, hydroxyl and N-acetyl groups through chemical reactions, such as esterification, acylation, amidation, and sulphation. An example of an esterified-HA is a product sold under the tradename HYAFF 11 (Fidia Advanced Biopolymers, Abano Terme, Italy), which has all of its carboxyl groups esterified with benzyl esters. This material is stable in aqueous media for a few weeks, but completely degrades within 2 months.

In many tissue repair applications, e.g. musculoskeletal tissue repair and/or regeneration, the scaffold must be structurally intact for periods far longer than two months. While the use of HA in tissue repair is desired due to HA's function in extracellular matrices and its recognition by certain cell receptors that regulate attachment, proliferation, differentiation and matrix synthesis of certain cell types, thus far approaches using natural HA or known modified-HA have proven inadequate to provide tissue scaffolds that maintain the structural integrity for extended periods of time that is necessary in applications such as musculoskeletal tissue repair or regeneration. The inventions described herein provide a solution to the need for such tissue scaffolds.

SUMMARY OF THE INVENTION

The present invention is directed to a tissue scaffold suitable for use in repair and/or regeneration of musculoskeletal tissue. The scaffold comprises a biodegradable, porous substrate comprising a biodegradable, hydrophobic polymer and a hyaluronic acid complex incorporated with the substrate, wherein the hyaluronic acid complex is insoluble in water, yet soluble in mixtures of organic and aqueous solvents in which the selected hydrophobic polymer is soluble. The structures of the substrates in the present invention may be nonwoven, fibrous mats or porous foams. The nonwoven, fibrous mats comprise fiber composed of biodegradable, hydrophobic polymers. The foams also are composed of biodegradable, hydrophobic polymers. The hyaluronic acid complex may be dispersed and incorporated on surface(s) of the substrate and/or dispersed and incorporated throughout the substrate.

BRIEF DESCRIPTION OF THE FIGURES

FIG. 3 shows Safranin-O (SO) histological sections (100×) of a tissue scaffold of the present invention including cultured bovine chondrocytes.

DETAILED DESCRIPTION OF THE INVENTION

Figure 1:
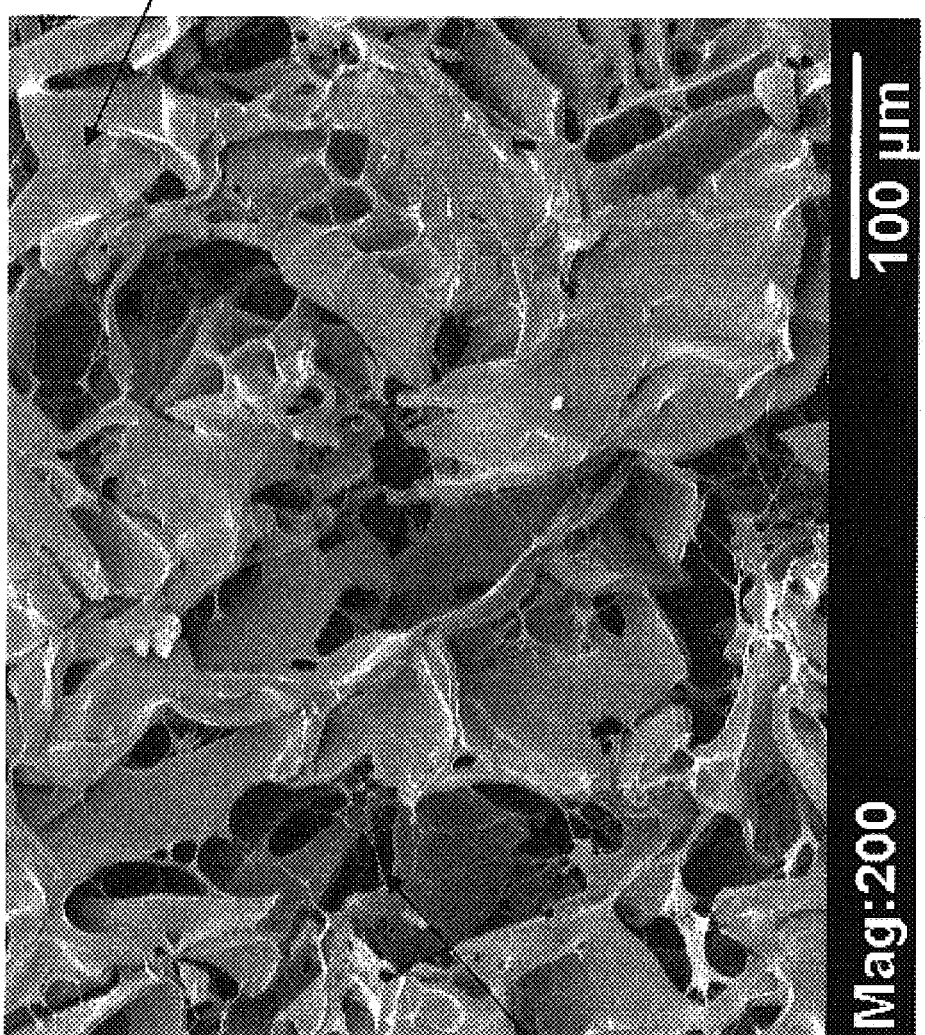
FIG. 1 is a scanning electron micrograph(SEM) cross-sectional image of a tissue scaffold of the present invention.

In treatments such as musculoskeletal tissue repair and/or regeneration, tissue scaffolds must maintain their physical and structural integrity once implanted into the body for extended periods of time, e.g. greater than two months, as compared to other treatments, e.g. corneal transplantation, viscosupplementation of the knee, anti-adhesive barriers in spinal surgeries and wound healing applications, where such long-term properties are not required. In addition, in order to provide such long-term tissue scaffolds with long-term enhanced cell-growth properties, hyaluronic acid (HA) material also must be able to remain incorporated with the scaffold for similar extended periods of time. Hydrophilic HA materials will dissipate relatively quickly when exposed to fluids of the body when implanted therein. As such, hydrophilic HA materials are not successful candidates for use in tissue scaffolds intended for use in applications requiring physical integrity over extended periods of time.

In order to circumvent the shortcomings of tissue scaffolds using unmodified HA or hydrophilic modified HA, this invention utilizes a structurally robust scaffold based on a porous substrate made from biodegradable, hydrophobic polymers and a relatively hydrophobic HA complex, as further described herein, distributed and incorporated on and/or throughout the scaffold. The hydrophobic HA complexes used in the present invention are more compatible with the hydrophobic polymers than unmodified HA.

As will be noted herein, the HA complex should be distributed on the surfaces of and/or throughout the porous substrate to obtain optimum cell-growth properties in the tissue scaffold. In addition, the HA complex is incorporated with the porous substrate, such that HA complex is bound to the porous substrate and not readily removable from the substrate once implanted in the body.

In one embodiment, tissue scaffolds of the present invention utilize an HA complex that can be dissolved in an aqueous/organic solvent mixture and blended with a solution of the hydrophobic polymer in an appropriate organic solvent. The blend of the dissolved HA complex and hydrophobic polymer subsequently can be lyophilized to generate a porous foam tissue scaffold having the HA complex dispersed and incorporated throughout the foam scaffold substrate. Alternatively, the HA complex of the present invention can be dissolved in an organic/aqueous mixture that subsequently can be poured over a hydrophobic substrate, e.g. a fibrous, nonwoven mat, allowed to penetrate the substrate, and then lyophilized to yield a substrate having the HA complex tightly adhered thereto.

As noted above, native HA is a hydrophilic, highly water-soluble material. Therefore, in order to be used in the present invention, native HA must be modified in order to make it more compatible with hydrophobic, polymers utilized in the present invention. The HA complex of the present invention is insoluble in water and shows improved solubility in selected organic solvents and organic/aqueous solvent blends as compared to native HA or hydrophilic modified HA. It is this characteristic of the modified HA that allows it to be more compatible with hydrophobic polymers as compared to highly hydrophilic native HA.

To achieve this compatibility, native HA was modified by two methods. In the first method, a macromolecular salt complex of HA was formed via the ion-exchange of alkali metal monovalent salt of HA, for example sodium hyaluronate (HA-Na) or potassium hyaluronate (K-HA), and a tetra alkyl ammonium halide. Tetra alkyl ammonium halides useful in the present invention may be represented as below.

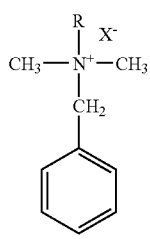

where R is $C_8H_{17}$ to $C_{18}H_{37}$ and X is Cl or Br.

In the second method, water-insoluble complexes of HA were formed by modifying HA-Na with organic halides, including but not limited to palmitoyl chloride, acetyl chloride, acetoxyacetyl chloride, ethyl 4-chloro-4-oxo-butyrate and acryloyl chloride, in the presence of organic base HCL acceptors such as triethylamine or pyridine. These modified HA complexes are soluble or partially soluble in certain organic solvents and mixtures of organic/aqueous solvents.

Method A

The first approach involves an ion-exchange route between the monovalent alkali metal hyaluronate and tetra alkyl ammonium halides, as represented above. This reaction occurs by the ion-exchange of the negatively charged carboxylate groups of the alkali metal hyaluronate, e.g. HA-Na or HA-K, with the positively charged tetra alkyl ammonium halides, resulting in the formation of an HA complex with a difference in solubility as compared to unmodified HA. The tetra alkyl ammonium halides used in this invention are soluble in both water and organic solvents, such as alcohols, acetone, 1,4-dioxane and tetrahydrofuran.

Halides that can be used in this invention include, but are not limited to, tetrabutylammonium bromide, cetyldimethylethylammonium bromide, benzalconium chloride, stearyldimethylbenzylammonium chloride, 3-(benzyldimethylammonio)propanesulfonate, benzyldimethyldecylammonium chloride, benzyldimethyldodecylammonium bromide, benzyldimethyldodecylammonium chloride, benzyldimethylhexadecylammonium chloride, benzyldimethyl(2-hydroxyethyl)ammonium chloride, benzyldimethyltetradecylammonium chloride, and benzethonium chloride.

The preferred tetra alkyl ammonium halide is benzalconium chloride (BzCl), a white or yellowish-white solid in the form of an amorphous powder or gelatinous pieces. The chemical scheme for forming a complex between HA-Na and BzCl is shown below.

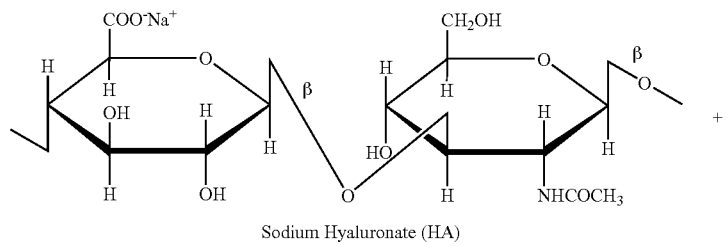

Sodium Hyaluronate (HA)

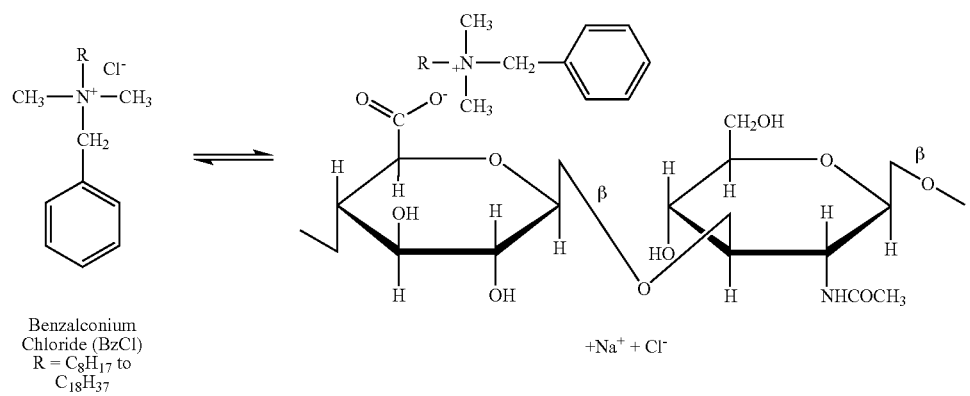

Benzalconium Chloride (BzCl)
R = $C_8H_{17}$ to $C_{18}H_{37}$ $+Na^+ + Cl^-$

BzCl has been investigated previously as an antimicrobial agent and shown to be safe at concentrations up to 0.1% weight. BzCl is a mixture comprised of alkyldimethylbenzylammonium chlorides.

Three major homologues include $C_{12}$, $C_{14}$ and $C_{16}$ straight chain alkyls. The combination of aliphatic hydrocarbon chains and positively charged ammonium groups imparts facile dissolution in both water and select organic solvents.

An added advantage of the present HA complex is that by changing the ratio of the hyaluronate, e.g. HA-Na, to BzCl, the solubility of the complex can be changed in a buffered solution.

Method B

The second approach involves the covalent modification of the hydroxyl and/or carboxylate groups of the monovalent salt, e.g. HA-Na or HA-K, with organic halides in the presence of bases such as triethylamine or pyridine. The chemical scheme for forming a covalent modification of HA-Na with organic halides is shown below.

plexes prepared according to method A or B is a blend of organic solvents such as 1,4-dioxane, dimethyl sulfoxide (DMSO), N,N-dimethylacetamide (DMAC)), N,N-dimethylformamide (DMF), and methylene chloride and water. The HA complex formed according to the methods of this invention is not completely soluble in aprotic nonpolar solvents or pure water. The preferred solvent system for method A is a 60/40 blend of 1,4-dioxane/water. The preferred solvent system for method B is DMSO using 5 percent by weight tetrabutylammonium bromide as a phase transfer agent.

In another embodiment of the present invention, the solubility of the HA complex can be varied either by changing the ratio of HA-Na to BzCl in method A or by changing the acid halide in method B. Complexes containing 1:1 molar ratios of HA:BzCl ultimately dissolve in aqueous environments slower than complexes comprised of 1:0.5 or 1:0.25. At all of these ratios the complexes are less soluble in an aqueous environment as compared to unmodified HA. The ultimate dissolution of such a complex is primarily through dissocia-

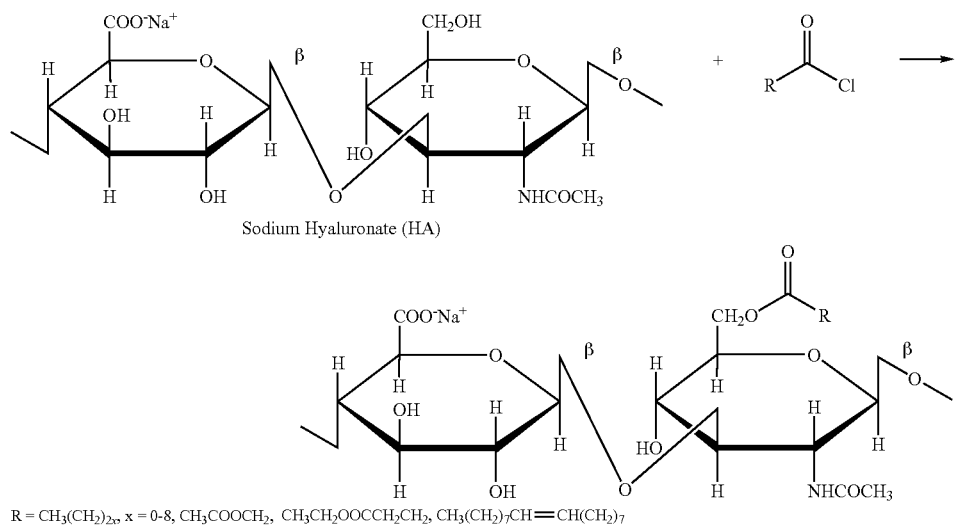

R = $CH_3(CH_2)_{2x}$, x = 0-8, $CH_3COOCH_2$, $CH_3CH_2OOCCH_2CH_2$, $CH_3(CH_2)_7CH{=}CH(CH_2)_7$

The reaction conditions employed results in partial substitution of the hydroxyl or carboxylate groups of HA. This renders the modified HA complex insoluble in water and soluble in organic solvents such as DMSO and aqueous/organic mixtures. The preferred organic halides include, but are not limited to, palmitoyl chloride, acetyl chloride, acetoxyacetyl chloride, ethyl 4-chloro-4-oxo-butyrate, acryloyl chloride, butyryl chloride, stearoyl chloride, myristoyl chloride, lauroyl chloride, oleoyl chloride, caproyl chloride and decanoyl chloride.

The organic base is selected from the group consisting of triethylamine, pyridine, trimethylamine, lutidine, quinoline, piperidine and pyrrolidine. The choice of the organic halide, organic base, solvent, temperature, and reaction times will determine the degree of substitution and, in turn, the solubility of the modified HA complex in organic solvents. One skilled in the art, once having the benefit of this disclosure, will be able to readily ascertain the particular elements and conditions of such reactions based on the desired result.

The source of HA-Na for either of the two methods listed above can be either animal-derived or obtained by bacterial fermentation. The preferred solvent system for HA comtion of HA and BzCl units. By using one or a combination of more than one of the methods described herein, one skilled in art can appreciate that the dissolution rate of the HA complex of the present invention can be tailored to match the kinetics of tissue repair.

The biodegradable, hydrophobic polymer of the present invention is selected from the group consisting of aliphatic polyesters, poly(amino acids), polyalkylene oxalates, polyamides, tyrosine-derived polycarbonates, polyorthoesters, polyoxaesters, poly(anhydrides), polyphosphazenes and biopolymers, e.g. collagen, elastin and bioabsorbable starches and blends thereof. Preferred are the synthetic polymers.

Currently, aliphatic polyesters are among the preferred synthetic, biodegradable, hydrophobic polymers of the present invention. Aliphatic polyesters can be homopolymers, copolymers (random, block, segmented, tapered blocks, graft, triblock, etc.) having a linear, branched or star structure. Suitable monomers for making aliphatic homopolymers and copolymers may be selected from the group consisting of, but are not limited to, lactic acid, lactide (including L-, D-, meso and D,L mixtures), glycolic acid, glycolide, epsilon-caprolactone, para-dioxanone (1,4-dioxan-2-one) and trimethylene carbonate (1,3-dioxan-2-one).

Synthetic, biodegradable, hydrophobic elastomeric copolymers are also particularly useful in the present invention. Suitable elastomeric polymers include those with an inherent viscosity in the range of 1 dL/g to 4 dl/g, preferably about 1 dL/g to 2 dL/g and most preferably about 1 dL/g to 1.7 dL/g, as determined at 25° C. in a 0.1 gram per deciliter (g/dL) solution of polymer in hexafluoroisopropanol (HFIP). For the purpose of this invention, an "elastomeric copolymer" is defined as a polymer that, at room temperature, can be stretched repeatedly to at least twice its original length and which, upon immediate release of stress, will return to approximately its original length.

Exemplary synthetic, biodegradable, hydrophobic elastomeric copolymers include, but are not limited to, copolymers of epsilon-caprolactone (PCL) and glycolide (including polyglycolic acid (PGA)) with a mole ratio of epsilon-caprolactone to glycolide of from about 35/65 to about 65/35, more preferably from 45/55 to 35/65; copolymers of epsilon-caprolactone and lactide (PLA) where the mole ratio of epsilon-caprolactone to lactide is from about 30/70 to about 95/5 and more preferably from 30/70 to 45/55 or from about 85/15 to about 95/5; copolymers of para-dioxanone (PDS) and lactide where the mole ratio of para-dioxanone to lactide is from about 40/60 to about 60/40; copolymers of epsilon-caprolactone and para-dioxanone where the mole ratio of epsilon-caprolactone to para-dioxanone is from about 30/70 to about 70/30; and blends thereof.

The preferred synthetic biodegradable, hydrophobic polymers and copolymers for the present invention are 90/10 PGA/PLA, PDS, 65/35 PGA/PCL, 60/40 PLA/PCL, 85/15 PLA/PCL, 95/5 PLA/PGA and blends thereof.

The synthetic biodegradable, hydrophobic polymer of the present invention can be prepared in the form of a scaffold component by a number of methods known in the art. If fibrous, the synthetic biodegradable, hydrophobic polymer may be extruded into fibers and the fibers then may formed into a porous, fibrous nonwoven structure using standard wet-lay or dry-lay techniques.

Alternatively, the synthetic scaffold component of this invention can be prepared in the form of a porous, sponge or foam structure by a variety of techniques well known to those having ordinary skill in the art. For example, the hydrophobic polymer may be dissolved in an appropriate solvent for the polymer and then processed into a foam by lyophilization, supercritical solvent foaming, gas injection extrusion, gas injection molding or casting with an extractable material (e.g., salts, sugar or similar suitable materials).

In one embodiment, the foam substrate component of the present invention can be made by a polymer-solvent phase separation technique, such as lyophilization.

The steps involved in the preparation of these synthetic foams include choosing the appropriate solvents for the polymers to be lyophilized and preparing a homogeneous solution of the polymer in the solution. The polymer-solvent solution then is subjected to a freezing and a vacuum drying cycle. The freezing step phase-separates the solution and the vacuum drying step removes the solvent by sublimation and/or drying, thus leaving a porous polymer structure, or an interconnected, open-cell porous foam.

Suitable solvents that may be used in the preparation of the porous foam substrate include, but are not limited to, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, methylethyl ketone, dipropyleneglycol methyl ether, 1,4-dioxane, 1,3-dioxolane, ethylene carbonate, dimethlycarbonate, benzene, toluene, benzyl alcohol, p-xylene, naphthalene, N-methylpyrrolidone, dimethylformamide, chloroform, 1,2-dichloromethane, dimethylsulfoxide, and mixtures thereof. Among these solvents utilized in preferred embodiments of the invention, a preferred solvent is 1,4-dioxane. A homogeneous solution of the polymer in the solvent is prepared using standard techniques.

In one embodiment, additional solids may be added to the polymer-solvent system to modify the composition of the resulting foam substrate. As the added particles settle out of solution, the added solids may be more concentrated in desired regions (i.e., near the top, sides or bottom) of the resulting tissue implant, thus causing compositional changes in such regions where desired for a particular purpose.

A variety of types of solids can be added to the polymer-solvent system. Preferably, the solids are of a type that will not react with the polymer or the solvent. Generally, the added solids have an average diameter of less than about 1 mm and preferably will have an average diameter of from about 50 to about 500 microns. When utilized, preferably the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, calcium carbonate particles for bone repair, solids that will render the scaffold radio opaque, leachable solids for pore creation, and particles that are effective as reinforcing materials.

Suitable leachable solids include nontoxic leachable materials such as salts, biocompatible mono and disaccharides, polysaccharides, or water soluble proteins. The leachable materials can be removed by immersing the foam substrate with the leachable material in a solvent in which the particle is soluble for a sufficient amount of time to allow leaching of substantially all of the particles, but which does not dissolve or detrimentally alter the foam substrate.

Suitable non-bioabsorbable materials include biocompatible metals or bioinert ceramic particles. Further, the non-bioabsorbable materials may include polymers such as polyethylene, polyvinylacetate, polymethylmethacrylate, silicone, polyethylene oxide, polyethylene glycol, polyurethanes, natural biopolymers, and fluorinated polymers and copolymers.

In addition, effectors, including drugs, bioactive molecules or cells, such as platelet rich plasma, bone marrow cells, and a combination of the two, can be added or injected into the tissue scaffold at the point of care.

In an alternative embodiment of the invention, the tissue scaffold may be modified either through physical or chemical means to contain biological or synthetic factors or agents that promote attachment, proliferation, differentiation and matrix synthesis of targeted cell types. Furthermore, the bioactive factors may also comprise part of the scaffold for controlled release of the factor to elicit a desired biological function. Another embodiment would include delivery of small molecules that affect the up regulation of endogenous growth factors. Growth factors, extracellular matrix proteins, and biologically relevant peptide fragments that can be used with the matrices of the current invention include, but are not limited to, antibiotics and antiviral agents; anticancer agents; anti-rejection agents; analgesics and analgesic combinations; anti-inflammatory agents such as acetaminophen; cytostatic agents such as Rapamycin; hormones such as steroids; analgesics; growth factors, including bone morphogenic proteins (BMP-2, BMP-4, BMP-6, BMP-12, BMP-2); sonic hedgehog; growth differentiation factor (GDF5, GDF6 and GDF8); epidermal growth factor; fibroblast growth factor; platelet derived growth factor (PDGF); insulin like growth factor (IGF-I and IGF-II); transforming growth factors (TGF-β I-III); parathyroid hormone, vascular endothelial growth factor (VEGF); genetically engineered cells that express desired proteins; and other naturally derived or genetically engineered proteins, polysaccharides, glycoproteins, or lipoproteins. The biological factors may be obtained either through a commercial source or isolated and purified from a tissue.

In yet another alternative embodiment, the tissue scaffolds of the present invention can be seeded or cultured with appropriate cell types prior to implantation. Cells which can be seeded or cultured on the scaffolds of the current invention include, but are not limited to, bone marrow cells, mesenchymal stem cells, stromal cells, stem cells, embryonic stem cells, chondrocytes, osteoblasts, precursor cells derived from adipose tissue, bone marrow derived progenitor cells, kidney cells, intestinal cells, islets, sertoli cells, peripheral blood progenitor cells, fibroblasts, keratinocytes, nucleus pulposus cells, anulus fibrosis cells, fibrochondrocytes, stem cells isolated from adult tissue, neuronal stem cells, glial cells, macrophages and genetically transformed cells or combination of the above cell. The cells can be seeded on the scaffolds of the present invention for a short period of time, e.g. less than one day, just prior to implantation, or cultured for a longer (>1 day) period, e.g. greater than one day, to allow for cell proliferation and matrix synthesis within the seeded scaffold prior to implantation.

The scaffold configuration must be effective to facilitate tissue ingrowth. A preferred tissue ingrowth-promoting configuration is one where the cells of the scaffold are open and of sufficient size to permit cell growth therein. An effective pore size is one in which the pores have an average diameter in the range of from about 20 to about 1,000 microns, more preferably, from about 20 to about 500 microns.

The following examples are illustrative of the principles and practice of the invention, although not intended to limit the scope of the invention. Numerous additional embodiments within the scope and spirit of the invention will become apparent to those skilled in the art.

EXAMPLE 1

This example describes several procedures used to make HA-BzCl complexes according to method A.

Equimolar amounts of sodium hyaluronate (1.5 gm) and benzalconium chloride (1.3 gm) were mixed together in distilled water. After 1 hour of stirring at 25° C., the precipitated solid was filtered and vacuum dried overnight, yielding 1:1 molar HA-BzCl complex.

In a similar manner, 2:1 and 4:1 molar HA-BzCl complexes were made, except the amount of benzalconium chloride was changed from (1.3 gm) for the 1:1 molar HA-BzCl complex, to 0.65 gm and 0.33 gm of benzalconium chloride for the 2:1 and 4:1 molar HA-BzCl complexes, respectively.

An alternate procedure to form 1:1 HA-BzCl complex was also used. Sodium hyaluronate (1.5 gm) was added to a solution containing benzalconium chloride (1.3 gm) in a mixture of 1,4-dioxane (118 gm) and water (78.5 gm). The solution was stirred for 24 hours at 25° C. and centrifuged for 1 hour at a rate of 4,000 rpm using an Eppendorf Centrifuge 5810R. Residual NaCl was removed by dialysis.

EXAMPLE 2

This example describes the process of making a water-insoluble HA complex according to method B.

Triethyl amine (8.3 gm) was added to a mixture containing sodium hyaluronate (500 milligram) in anhydrous N,N-dimethylformamide (250 gm). The mixture was cooled to 0° C. and palmitoyl chloride (23 gm) was added drop-wise. The resultant suspension was heated to 45° C. and stirred for 20 hours. The suspension was poured into dialysis tubing (12,000-14,000 molecular weight cut-off) and dialyzed against methanol and isopropanol for 2 weeks. Contents inside the dialysis membrane were reduced by rotary evaporation and vacuum dried overnight, yielding 1.5 gm of a white powder.

EXAMPLE 3

This example describes the stability of the HA-BzCl complex fabricated according to Example 1, in distilled water or aqueous buffer solution.

First, 250 milligrams of 1:1 HA-BzCl complex made in Example 1 was suspended in 20 grams of distilled water and stirred for 2 weeks at 25° C. The remaining solid was vacuum dried at 40° C. for 48 hours using phosphorous pentoxide drying agent to yield 55 milligram of a white solid. This represents a 78 percent loss of the starting mass of 1:1 HA-BzCl complex.

In a second experiment, 72 milligrams of 1:1, 2:1, and 4:1 HA-BzCl complex made in Example 1 were each suspended in PBS solution (pH 7.4, 37° C.) and shaken in a constant temperature water bath. The degradation of the HA-BzCl was monitored by measuring the absorbance peaks corresponding to HA and BzCl at 205 nm and 262 nm, respectively, using a UV/Vis spectrometer. Calibration curves were generated using pure HA and BzCl dissolved in PBS. The results indicated that 100 percent of the 4:1 HA-BzCl degraded after 1 day, 100 percent of the 2:1 HA-BzCl complex degraded after 4 days, and 70 percent of the 1:1 HA-BzCl complex degraded after 2 weeks.

EXAMPLE 4

This example describes the process of incorporating the HA-BzCl complex described in Example 1 into a porous, foam substrate prepared from a hydrophobic polymer.

The foam substrate was prepared utilizing a copolymer of 65/35 PGA/PCL produced by Birmingham Polymers Inc. (Birmingham, Ala.) with an I.V. of 1.79 dL/g, as measured in HFIP at 30° C. The foam was fabricated using a lyophilization procedure as described herein.

A solution of 0.1 weight percent of HA-BzCl solution in a 60/40 1,4-dioxane/water mixture was prepared.

A laboratory scale lyophilizer (Model Duradry, from FTS Kinetics, Stone Ridge, N.Y.), was used in this example. The synthetic foam substrate (70 mm×70 mm×2 mm) composed of 65/35 PGA/PCL was placed in a 4-inch×4-inch aluminum mold. The HA-BzCl polymer solution was added to the mold such that the solution covered the foam substrate such that the substrate was submersed in the solution.

The mold assembly then was placed on the shelf of the lyophilizer and the freeze-dry sequence begun. The freeze-dry sequence used in this example was: 1) −17° C. for 60 minutes; 2) −5° C. for 60 minutes under vacuum 100 mT; 3) 5° C. for 120 minutes under vacuum 20 mT; 4) 20° C. for 120 minutes under vacuum 20 mT.

After the cycle was completed, the mold assembly was removed from the lyophilizer and allowed to degas in a vacuum hood for 2 to 3 hours. The tissue scaffold comprising the substrate and the incorporated Ha-BZ was taken from the mold and stored under nitrogen.

FIG. 1 is a scanning electron micrograph (SEM) of a cross-section of the foam tissue scaffold. The SEM shows the lyophilized HA-BzCl 5 incorporated within and dispersed the foam tissue scaffold 10.

EXAMPLE 5

This example describes the process of incorporating the HA-BzCl complex described in Example 1 within a synthetic, porous, nonwoven substrate.

The laboratory scale lyophilizer from Example 4 was used in this example. Three sheets of a synthetic nonwoven substrate (70 mm×70 mm×2 mm) composed of 90/10 PGA/PCL fibers were prepared and placed in 4-inch×4-inch aluminum molds. Three solutions of HA-BzCl in 60/40 1,4-dioxane/water mixture were prepared with 0.05, 0.10, and 0.25 weight percent HA-BzCl, respectively. The three solutions were added to the three molds such that the substrates were immersed in the solutions.

The mold assemblies were placed on the shelf of the lyophilizer and the freeze-dry sequence begun. The freeze-dry sequence used in this example was the same as used in Example 4.

After the cycle was completed, the mold assemblies were removed from the lyophilizer and allowed to degas in a vacuum hood for 2 to 3 hours. The tissue scaffolds were taken from the mold and stored under nitrogen.

Figure 2:
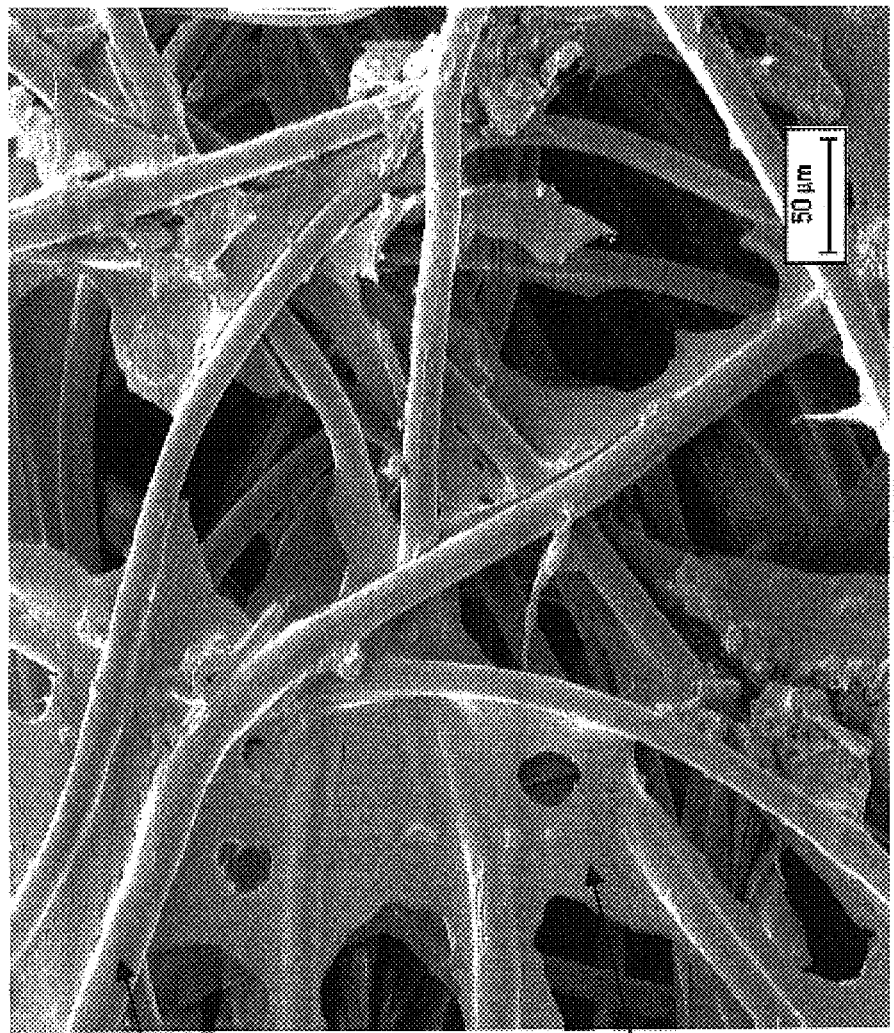
FIG. 2 is a SEM cross-sectional image of a tissue scaffold of the present invention.

The resulting tissue scaffolds contained the nonwoven substrate having the HA-BzCl dispersed there through. FIG. 2 is a scanning electron micrograph (SEM) of a cross-section of the nonwoven tissue scaffold. The SEM clearly shows the lyophilized Ha-BzCl 15 incorporated with the synthetic fibers 20 of the nonwoven substrate.

EXAMPLE 6

This example illustrates that chondrocytes proliferate and synthesize a proteoglycan-rich matrix within the tissue scaffolds described in Example 4. Specifically, the 90/10 PGA/PCL nonwoven scaffolds comprising 0.05, 0.1, and 0.25 weight percent HA-BzCl complex in a 60:40 1,4-dioxane/water mixture from Example 5 were evaluated for chondrocyte response.

Primary chondrocytes were isolated from bovine shoulders as described by Buschmann, et al., in *J. Orthop. Res.*, 10, 745, (1992). Bovine chondrocytes were cultured in Dulbecco's modified eagles medium (DMEM-high glucose) supplemented with 10% fetal calf serum (FCS), 10 mM HEPES, 0.1 mM nonessential amino acids, 20 micrograms/ml L-proline, 50 micrograms/ml ascorbic acid, 100 U/ml penicillin, 100 microgram/ml streptomycin and 0.25 micrograms/ml amphotericin B (growth media). Half of the medium was replenished every other day.

The tissue scaffolds, cut to 5 mm in diameter and 1.5 mm thick, were sterilized for 20 minutes in 70 percent ethanol, followed by five rinses of phosphate-buffered saline (PBS).

Freshly isolated bovine chondrocytes were seeded at a density of $5 \times 10^6$ cells/scaffold in 24 well low cluster dishes, by adding a cell suspension (15 microliter) onto each scaffold. Cells were allowed to attach to the scaffold for three hours before addition of 1.5 ml of medium. Scaffolds were cultured for up to 1 week in a humidified incubator at 37° C. in an atmosphere of 5 percent $CO_2$ and 95 percent air. Half of the medium was replaced every other day.

Scaffolds were harvested at 1 and 7 days, and evaluated for histological staining. At each time point, three samples were fixed in 10 percent buffered formalin, embedded in paraffin and sectioned using a Zeiss Microtome. Cell distribution within tissuescaffolds was assessed by hematoxylin staining of cross sections of scaffolds 24 hours after cell seeding. Furthermore, sections were also stained for the presence of sulfated proteoglycans Safranin-O (SO; sulfated GAG's). Computer images were acquired using a Nikon Microphot-FXA microscope fitted with a Nikon CCD video camera (Nikon, Japan).

FIG. 3 shows SO histological sections (100×) of the 0.05 and 0.1 weight percent HA-BzCl-impregnated nonwoven tissue scaffolds cultured with bovine chondrocytes for 1 week. The figures show cell attachment, proliferation, and matrix formation in each of the scaffolds.

EXAMPLE 7

This example describes the process of forming a porous, foam tissue scaffold from a solution comprising a blend of HA-BzCl (1:1 molar ratio) complex with a synthetic, biodegradable, hydrophobic polymer.

A solution of 0.10 weight percent of HA-BzCl (1:1) solution in a 60/40 dioxane/water mixture was prepared and mixed in a 1:9 volume ratio with a 5% 65/35 PGA/PCL solution in 1,4-dioxane, poured into an aluminum mold and immediately placed over a liquid nitrogen bath for 5 minutes to freeze the solution. The mold was transferred to a laboratory scale lyophilizer and lyophilized according to the protocol outlined in Example 4.

After the cycle was completed, the mold assembly was removed from the lyophilizer and allowed to degas in a vacuum hood for 2 to 3 hours. The scaffold was taken from the mold and stored under nitrogen.

The following tables represent the relative solubility behavior of Ha-Bz complexes prepared according to the invention in mixtures of 1,4-dioxane/water and DMAC/water, respectively.

TABLE 1

Room Temperature Solubility of HA:BzCl in Dioxane/Water.

| HA:BzCl Mole Ratio | HA Weight % | Dioxane/$H_2O$ (w/w) | Ha:BzCl Solubility |
|---|---|---|---|
| 1:1 | 1 | 0/100 | No |
| 1:1 | 0.5 | 0/100 | No |
| 1:1 | 0.25 | 0/100 | No |
| 1:1 | 1 | 50/50 | Yes |
| 1:1 | 1 | 70/30 | No |
| 1:1 | 1 | 65/35 | Partially |
| 1:1 | 0.5 | 70/30 | No |
| 1:1 | 0.5 | 65/35 | Partially |
| 1:1 | 0.5 | 60/40 | Yes |
| 1:1 | 0.5 | 50/50 | Yes |
| 1:1 | 0.25 | 50/50 | Yes |
| 1:1 | 1 | 75/25 | No |
| 1:1 | 0.5 | 75/25 | No |
| 1:1 | 0.25 | 75/25 | No |
| 1:1 | 0.25 | 100/0 | No |
| 1:0.5 | 1 | 0/100 | No |
| 1:0.5 | 0.5 | 0/100 | No |
| 1:0.5 | 0.25 | 0/100 | No |
| 1:0.5 | 1 | 50/50 | Yes |
| 1:0.5 | 0.5 | 50/50 | Yes |
| 1:0.5 | 0.25 | 50/50 | Yes |
| 1:0.5 | 1 | 75/25 | No |
| 1:0.5 | 0.5 | 75/25 | No |
| 1:0.5 | 0.25 | 75/25 | No |
| 1:0.5 | 0.25 | 100/0 | No |

HA = sodium hyaluronate derived from bacterial fermentation (~450 000 Da)
BzCl = benzalconium chloride

TABLE 2

Room Temperature Solubility of HA:BzCl in DMAC/H₂O.

| HA:BzCl Mole Ratio | HA Weight % | DMAC/H₂O (w/w) | HA:BzCl Solubility |
|---|---|---|---|
| 1:1 | 1 | 25/75 | No |
| 1:1 | 0.5 | 25/75 | No |
| 1:1 | 0.25 | 25/75 | No |
| 1:1 | 0.25 | 100/0 | No |
| 2:1 | 1 | 100/0 | No |
| 2:1 | 0.5 | 100/0 | No |
| 2:1 | 0.25 | 100/0 | No |
| 2:1 | 1 | 60/40 | Yes |
| 2:1 | 1 | 50/50 | Yes |
| 2:1 | 0.5 | 50/50 | Yes |
| 2:1 | 0.25 | 50/50 | Yes |
| 2:1 | 1 | 25/75 | No |
| 2:1 | 0.5 | 25/75 | No |
| 2:1 | 0.25 | 25/75 | No |
| 2:1 | 0.25 | 0/100 | No |

HA = sodium hyaluronate derived from bacterial fermentation (~450 000 Da)
BzCl = benzalconium chloride

We claim:

1. A tissue scaffold suitable for use in repair and/or regeneration of musculoskeletal tissue when implanted in a body, comprising:
    a porous substrate comprising a biodegradable, hydrophobic polymer; and
    an alkali metal hyaluronate complex with either a tetraalkyl ammonium halide or an organic halide incorporated with said substrate,
wherein said alkali metal hyaluronate complex is insoluble in water, yet soluble in mixtures of organic and aqueous solvents in which said hydrophobic polymer is soluble.

2. The tissue scaffold of claim 1 wherein said substrate is selected from the group consisting of a foam and a fibrous, nonwoven mat.

3. The tissue scaffold of claim 2 wherein said biodegradable, hydrophobic polymer is selected from the group consisting of aliphatic polyesters, poly(amino acids), polyalkylene oxalates, polyamides, tyrosine-derived polycarbonates, polyorthoesters, polyoxaesters, polyphosphazenes, polyhydroxyalkanoates and biopolymers.

4. The tissue scaffold of claim 3 wherein said biodegradable, hydrophobic polymer comprises an aliphatic polyester.

5. The tissue scaffold of claim 4 wherein said aliphatic polyester is selected from the group consisting of homopolymers, copolymers and blends of poly(lactic acid), poly(glycolic acid), poly(epsilon-caprolactone), poly(dioxanone) and poly(trimethylene carbonate).

6. The tissue scaffold of claim 5 wherein said hyaluronate complex comprises a complex of sodium hyaluronate with benzalconium chloride in a molar ratio of from about 10:1 to 1:10.

7. The tissue scaffold of claim 6 wherein said hydrophobic polymer is selected from the group consisting of a copolymer of glycolide and lactide.

8. The tissue scaffold of claim 7 wherein said mixture of organic and aqueous solvents comprises a from about 70 percent to about 45 percent of said organic solvent and about 30 to about 55 percent of said aqueous solvent.

9. The tissue scaffold of claim 1 wherein said alkali hyaluronate complex is a complex of a monovalent alkali metal salt of hyaluronic acid with a tetra alkyl ammonium halide.

10. The tissue scaffold of claim 9 wherein said monovalent alkali metal salt of hyaluronic acid is selected from the group consisting of sodium hyaluronate and potassium hyaluronate.

11. The tissue scaffold of claim 10 wherein the molar ratio of said sodium hyaluronate to tetra alkyl ammonium halide is between about 10:1 and about 1:10

12. The tissue scaffold of claim 11 wherein said tetra alkyl ammonium halide is selected from the group consisting of tetrabutylammonium bromide, cetyldimethylethylammonium bromide, benzalconium chloride, stearyldimethylbenzylammonium chloride, 3-(benzyldimethylammonio)propanesulfonate, benzyldimethyldecylammonium chloride, benzyldimethyldodecylammonium bromide, benzyldimethyldodecylammonium chloride, benzyldimethylhexadecylammonium chloride, benzyldimethyl(2-hydroxyethyl)ammonium chloride, benzyldimethyltetradecylammonium chloride and benzethonium chloride.

13. The tissue scaffold of claim 1 wherein said hyaluronate complex is a complex of sodium hyaluronate with an organic halide.

14. The tissue scaffold of claim 13 wherein said organic halide is selected from the group consisting of palmitoyl chloride, acetyl chloride, acetoxyacetyl chloride, ethyl 4-chloro-4-oxo-butyrate, acryloyl chloride, stearoyl chloride, myristoyl chloride, lauroyl chloride, oleoyl chloride, caproyl chloride and decanoyl chloride.

15. The tissue scaffold of claim 1 further comprising cells seeded or cultured therewith prior to implantation in said body.

16. The tissue scaffold of claim 15 wherein said cells are selected from the group consisting of bone marrow cells, mesenchymal stem cells, stromal cells, embryonic stem cells, chondrocytes, osteoblasts, precursor cells derived from adipose tissue, bone marrow-derived progenitor cells, kidney cells, intestinal cells, islets, sertoli cells, peripheral blood progenitor cells, fibroblasts, keratinocytes, nucleus pulposus cells, anulus fibrosis cells, fibrochondrocytes, stem cells isolated from adult tissue, neuronal stem cells, glial cells, macrophages and genetically transformed cells.

17. The tissue scaffold of claim 1 further comprising biological or synthetic factors or agents that promote attachment, proliferation, differentiation or matrix synthesis of targeted cell types.

18. A tissue scaffold suitable for use in repair and/or regeneration of musculoskeletal tissue when implanted in a body, comprising:
    a porous substrate comprising a biodegradable, hydrophobic polymer; and
    an alkali metal hyaluronate complex with either a tetraalkyl ammonium halide selected from the group consisting of tetrabutylammonium bromide, cetyldimethylethylammonium bromide, benzalconium chloride, stearyldimethylbenzylammonium chloride, 3-(benzyldimethylammonio)propane-sulfonate, benzyldimethyldecylammonium chloride, benzyldimethyldodecyl ammonium bromide, benzyldimethyldodecylammonium chloride, benzyldimethylhexadecylammonium chloride, benzyldimethyl(2-hydroxyethyl)ammonium chloride, benzyldimethyltetradecylammonium chloride and benzethonium chloride, or an organic halide selected from the group consisting of palmitoyl chloride, acetyl chloride, acetoxyacetyl chloride, ethyl 4-chloro-4-oxo-butyrate, acryloyl chloride, stearoyl chloride, myristoyl chloride, lauroyl chloride, oleoyl chloride, caproyl chloride and decanoyl chloride incorporated with said substrate, wherein said alkali metal hyaluronate complex is insoluble in water, yet soluble in mixtures of organic and aqueous solvents in which said hydrophobic polymer is soluble.

* * * * *